United States Patent [19]

Gerhart et al.

[11] Patent Number: 4,914,240

[45] Date of Patent: Apr. 3, 1990

[54] GEM-DIHALO-1,8-DIAMINO-4-AZA-OCTANES

[75] Inventors: Fritz Gerhart, Kehl Leutesheim, Fed. Rep. of Germany; Pierre Mamont, Strasbourg, France

[73] Assignee: Merrell Dow Pharmaceuticals Inc., Cincinnati, Ohio

[21] Appl. No.: 330,663

[22] Filed: Mar. 30, 1989

Related U.S. Application Data

[62] Division of Ser. No. 62,302, Jun. 15, 1987, Pat. No. 4,851,448, which is a division of Ser. No. 767,928, Aug. 21, 1985, Pat. No. 4,695,654.

[51] Int. Cl.$^4$ ............................................. C07C 85/06
[52] U.S. Cl. .................................... 564/478; 564/510

[58] Field of Search ............................... 564/478, 510

[56] References Cited

U.S. PATENT DOCUMENTS 4,004,996 1/1977 Kollonitsch ...................... 564/510
4,089,903 5/1978 Whittle et al. ..................... 564/510

OTHER PUBLICATIONS

Danzig, M. et al, "The Preparation of Spermidine Trihydrochloride", J. Am. Chem. Soc., 74, 1936 (1952).

Primary Examiner—Richard L. Raymond
Attorney, Agent, or Firm—Raymond A. McDonald

[57] ABSTRACT

Gem-dihalo-1,8-diamino-4-aza-octane derivatives useful as antiproliferative or antitumor agents.

3 Claims, No Drawings

GEM-DIHALO-1,8-DIAMINO-4-AZA-OCTANES

CROSS-REFERENCE TO RELATED APPLICATION

This is a divisional of application Ser. No. 062,302, filed June 15, 1987, now U.S. Pat. No. 4,851,448 which is a divisional of application Ser. No. 767,928, filed Aug. 21, 1985, now U.S. Pat. No. 4,695,654.

BACKGROUND AND DESCRIPTION

It is a well known observation that the biosynthesis of natural polyamines, such as putrescine, spermidine and spermine, is elevated in rapidly proliferating cells relative to normal quiescent cells. Conversely, it is also known that the depletion of putrescine and spermidine leads to a reduction in cell proliferation.

Ornithine is the metabolic precursor of putrescine, which in turn, is the metabolic precursor of spermidine, which in turn, is the metabolic precursor of spermine. Metabolically, these biochemical conversions are catalysed by the enzymes ornithine decarboxylase, spermidine synthase and spermine synthase, respectively. Additionally, spermidine and spermine synthase enzymes utilize decarboxylatedS-adenoysl-L-methionine as a co-substrate, the reaction product of the S-adenosyl-L-methionine decarboxylase enzyme. Inhibitors of these enzymes, including inhibitors of S-adenosyl-L-methionine decarboxylase therefore, should serve to prevent the biosynthesis of putrescine and the higher polyamines derived therefrom, viz, spermidine and spermine, and should, theoretically, be effective as antiproliferative agents and and/or antitumor agents.

However, in the past, the use of irreversible ornithine decarboxylase inhibitors or inhibitors or S-adenosyl-L-methionine decarboxylase, spermidine synthase and spermine synthase have not proven to be totally effective. Thus, for example, putrescine and spermidine are not essential for the maintenance of cell viability as long as the preexisting spermine pool is maintained above a certain critical level. Moreover, a total in vivo inhibition of the decarboxylase enzymes is difficult due to their rapid turnover.

Applicants have discovered a class of compounds which deplete the natural levels of spermine in the cell. These compounds are highly effective inhibitors of cell growth in rapidly proliferating cells. Accordingly, the compounds of this invention are useful as antiproliferative and anti-tumor agents.

SUMMARY OF THE INVENTION

The present invention relates to certain selective gem-dihalo derivatives of spermidine. More particularly this invention relates to gem-dihalo-1,8-diamino-4-azaoctane derivatives having the formula

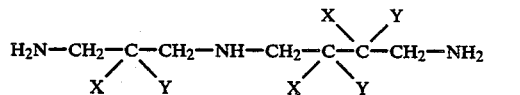

wherein X and Y represent hydrogen or halogen with the proviso that only two halogens are present on one and only one carbon atom at any given time; and the pharmaceutically acceptable salts thereof.

Additionally, certain aspects of this invention are directed to a process for the preparation of the compounds herein described, pharmaceutical compositions containing the same, and the use of these compounds as antitumor agents.

DETAILED DESCRIPTION OF THE INVENTION

As indicated in general formula (1) above the compounds of the present invention form a specific class of gem-dihalospermidines together with their pharmaceutically acceptable salts. As used throughout, however, a more definitive nomenclature will be employed, and the compounds will be designated as derivatives of gem-dihalo-1,8-diamino-4-aza-octanes. As used herein, the term halogen is intended to refer solely to the chloro and fluoro substituents.

All of the compounds encompassed within this invention are gem-dihalo derivatives. This is to say they are limited to either the 2,2-dihalo, 6,6-dihalo or 7,7-dihalo derivatives of 1,8-diamino-4-aza-octane, as indicated by the proviso limitation inserted in the claims. Thus, the compounds of this invention that are encompassed within the scope of claim 1 include:

2,2-difluoro-1,8-diamino-4-aza-octane
2,2-dichloro-1,8-diamino-4-aza-octane
2-chloro-2-fluoro-1,8-diamino-4-aza-octane
6,6-difluoro-1,8-diamino-4-aza-octane
6,6-dichloro-1,8-diamino-4-aza-octane
6-chloro-6-fluoro-1,8-diamino-4-aza-octane
7,7-difluoro-1,8-diamino-4-aza-octane
7,7-dichloro-1,8-diamino-4-aza-octane
7-chloro-7-fluoro-1,8-diamino-4-aza-octane.

The pharmaceutically acceptable salts include those non-toxic organic or inorganic acid addition salts of the base compounds of Formula (1) above. Illustrative inorganic acids include hydrochloric, hydrobromic, sulfuric and phosphoric acid as well as metal salts such as sodium monohydrogen orthophosphate and potassium hydrogen sulfate. Illustrative organic acids which form suitable salts include the mono, di and tricarboxylic acids, such as acetic, glycolic, lactic, pyruvic, malonic, succinic, glutaric, fumaric, malic, tartaric, citric, ascorbic, maleic, hydroxymaleic, benzoic, p-hydroxybenzoic, phenylacetic, cinnamic, salicyclic, 2-phenoxybenzoic and sulfonic acids such as methane sulfonic acid and 2-hydroxyethane sulfonic acid. Such salts can exist in either a hydrated or substantially anhydrous form.

All of the compounds of this invention are prepared in a logical sequence starting with the corresponding 2,2-dihalo-1,4-butanediols having the formula

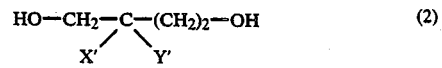

wherein X' and Y' represent chlorine or fluorine. These compounds are readily prepared by reacting the appropriate 2,2-dihalosuccinic acid with trifluoroacetic acid to form the corresponding 2,2-dihalosuccinic anhydrides. Cleavage of the anhydrides with methanol results in the formation of the corresponding methyl 2,2-dihalosuccinates. Reduction of the corresponding free acid function with borane-methyl sulfide complex results in the formation of the corresponding alcohols, i.e., the methyl 2,2-dihalo-4-hydroxybutanoates. Reduction of the ester function, for example using sodium borohydride, results in the formation of the desired starting materials; the 2,2-dihalo-1,4-butanediols (2).

The 6,6-dihalo and the 7,7-dihalo derivatives are prepared in accordance with the following synthetic pathway, wherein the symbols X' and Y' represent chlorine or fluorine, and the symbols X and Y represent hydrogen, chlorine or fluorine.

tained a mixture of 1-benzyloxy-2,2-dihalo-4-hydroxybutane (3a) and 1-benzyloxy-3,3-dihalo-4-hydroxybutane (3b). As used herein the symbol Bz represents the benzyl group.

This mixture of isomers can be readily separated by chromatography. If the 1-benzyloxy-2,2-dihalo-4-hydroxybutane isomer (3a) is utilized in the remaining reaction sequence, the gem-7,7-dihalo-1,8-diamino-4-

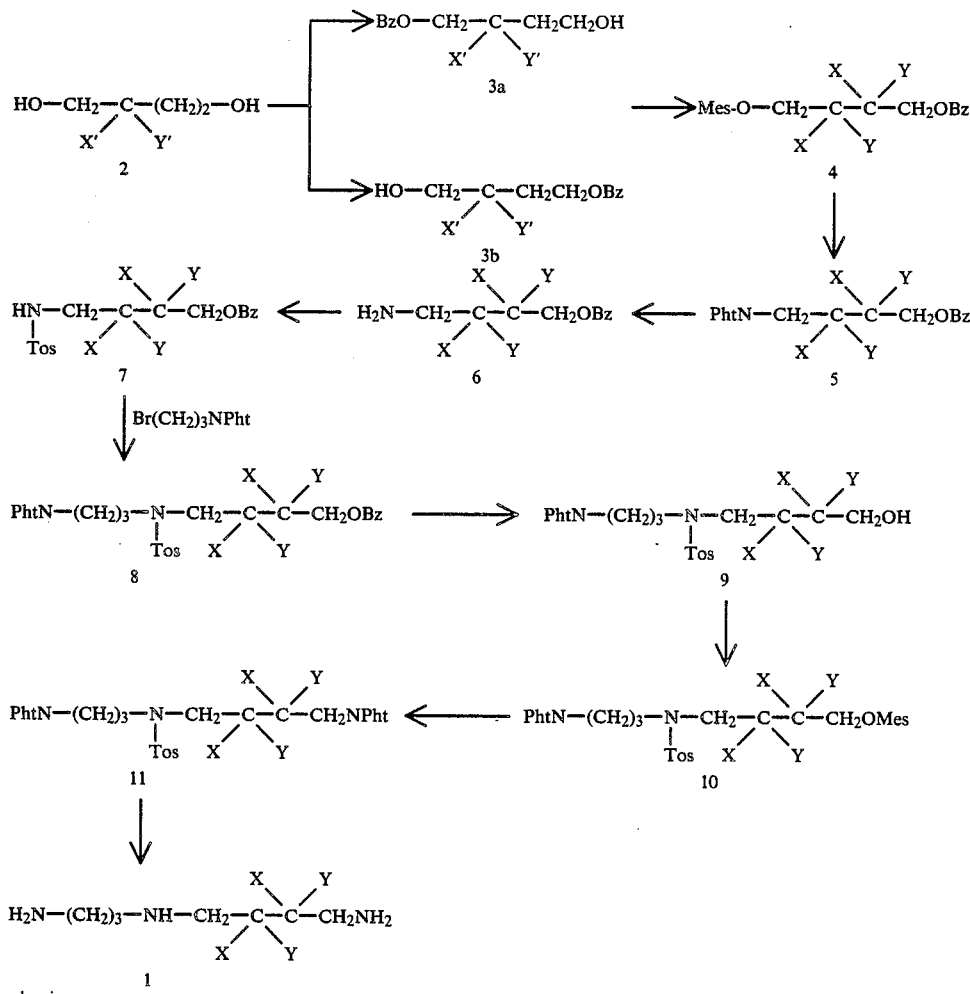

wherein:

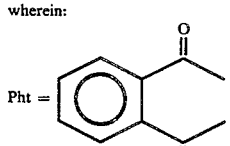

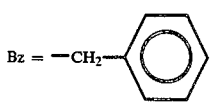

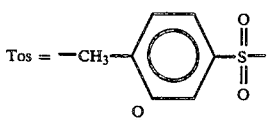

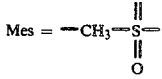

Controlled alkylation of the 2,2-dihalo-1,4-butanediol (2) by means of a benzylidene, such as benzyl bromide, in the presence of potassium tert-butoxide provides a suitable protecting form of the primary alcohols. Inasmuch as two primary alcohols are present, there is obaza-octanes are obtained. Conversely, if the 1-benzyloxy-3,3-dihalo-4-hydroxybutane isomer (3b) is utilized, the gem-6,6-dihalo-1,8-diamino-4-aza-octanes are obtained. Inasmuch as the reaction sequence is exactly the same, the general reaction scheme is indicated from this point on as being tetra-halo substituted, although in fact, only one of the carbon atoms is disubstituted at any given time.

The free hydroxyl group of the appropriate 1-benzyloxy-gem-dihalo-4-hydroxybutane can be protected utilizing methanesulfonyl chloride in an anhydrous, aprotic solvent, such as dichloromethane, to provide the corresponding 1-benzyloxy-gem-dihalo-4-methanesulfonyloxybutane (4). As used herein the symbol Mes represents the methanesulfonyl group. Reaction of (4) with potassium phthalimide in a solvent such as dimethylformamide results in the formation of the corresponding N-(4-benzyloxy-gem-dihalobutyl)phthalimide (5). The action of hydrazine in a solvent such as ethanol upon this phthalimide (5) provides the corresponding 4-benzyloxy-gem-dihalo-butylamine (6), which is best recovered as the hydrochloric salt.

To avoid obtaining a mixture of isomers in the subsequent alkylation step, the primary amine (6) is protected in a standard manner with p-toluenesulfonyl chloride to yield the corresponding N-(4-benzyloxy-gem-dihalobutyl)-p-toluenesulfonamide (7). Alkylation of the protected amine (7) with 3-bromopropylphthalimide under anhydrous conditions in a suitable aprotic solvent, such as dimethylformamide and in the presence of sodium iodide and potassium tert-butoxide, yields the corresponding 1-phthalimido-4-p-toluenesulfonyl-gem-dihalo-8-benzyloxy-4-aza-octane (8).

The corresponding 1-phthalimido-4-p-toluenesulfonyl-gem-dihalo-8-hydroxy-4-aza-octane (9) is prepared by cleaving the benzyl group of (8) with trimethylsilyl iodide. Reaction of (9) with methanesulfonyl chloride in the presence of pyridine in an anhydrous solvent such as dichloromethane results in the formation of the corresponding 1-phthalimido-4-p-toluenesulfonyl-gem-dihalo-8-methanesulfonyloxy-4-aza-octane (10).

Reaction of (10) with potassium phthalimide in anhydrous dimethylformamide results in the preparation of 1,8-diphthalimido-4-p-toluenesulfonyl-gem-dihalo-4-aza-octane (11). Heating (11) with hydrazine in a solvent such as ethanol serves to remove the phthaloyl protecting groups, whereas subsequently heating the product so obtained with aqueous HBr serves to remove the protecting tosyl moiety to yield the desired 6,6- or 7,7-dihalo-1,8-diamino-4-aza-octanes (1) as their hydrobromide salts.

The corresponding 2,2-dihalo derivatives are prepared in accordance with the following synthetic pathway, wherein X and Y shown below are in this case either chlorine or fluorine.

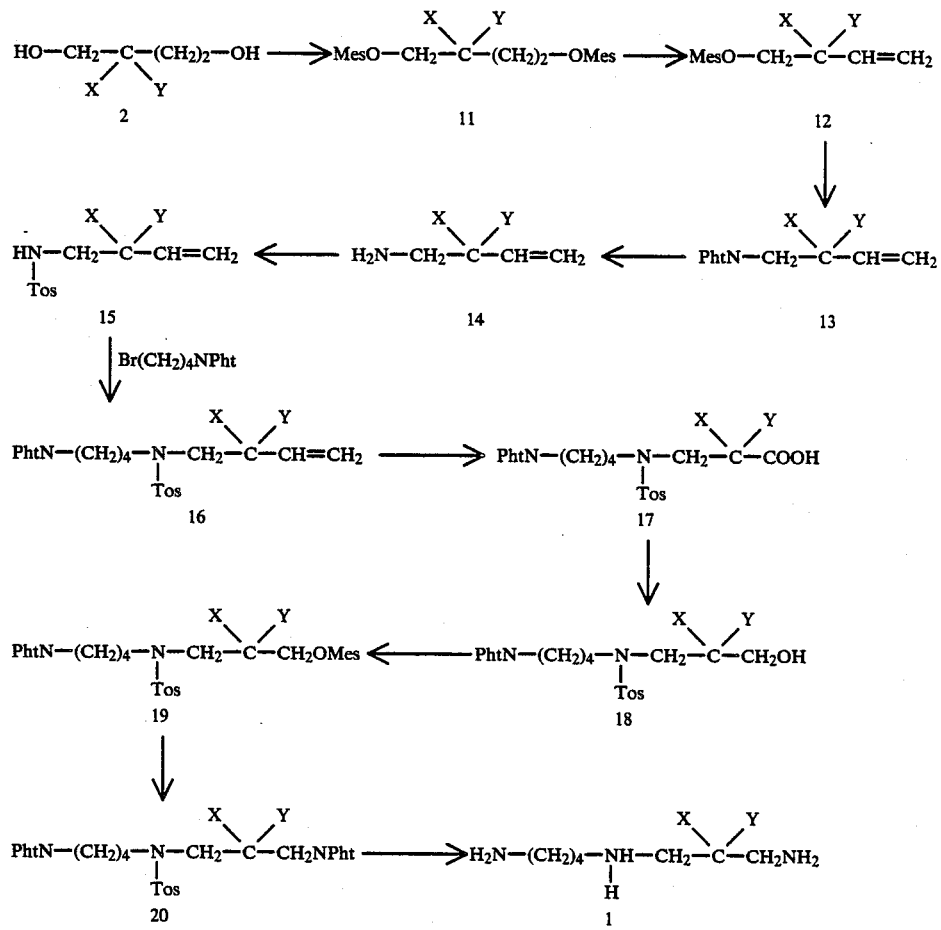

The 2,2-dihalo-1,4-butanediol (2) is treated with two equivalents of methanesulfonyl chloride in the presence of pyridine to form the corresponding 1,4-bis-methanesulfonyloxy-2,2-dihalobutane (11). When (11) is heated with diazabicycloundecen in a solvent such as dimethylformamide, there is obtained the corresponding 1-methanesulfonyloxy-2,2-dihalo-3-butene (12).

Reaction of (12) with potassium phthalimide in a solvent such as dimethylformamide results in the formation of the corresponding 1-phthalimido-2,2-dihalo-3-butene (13). Cleavage of the phthaloyl derivative (13) with hydrazine in an alcoholic solvent provides the corresponding 1-amino-2,2-dihalo-3-butene (14).

The primary amine (14) is protected by reaction with p-toluenesulfonyl chloride in a standard manner to obtain the corresponding N-(2,2-dihalo-3-butenyl)-p-toluenesulfonamide (15). Alkylation of the protected amine (15) with 4-bromobutylphthalimide in the presence of potassium tert.-butoxide under anhydrous conditions in a suitable solvent, such as dimethylformamide results in the formation of N-(4-phthalimidobutyl)-N-(2,2-dihalo-3-butenyl)-p-toluenesulfonamide (16).

Oxidation of the double bond with $KMnO_4$ in an aqueous acetic acid solution results in the corresponding (2,2-dihalo-8-phthalimido-4-p-toluenesulfonyl-4-aza-octanoic acid (17), which upon reduction with borane-methylsulfide complex forms the corresponding 2,2-dihalo-8-phthalimido-4-p-toluenesulfonyl-4-aza-octanol (18).

Reaction of (18) with methanesulfonyl chloride in the presence of pyridine utilizing an anhydrous solvent such as dichloromethane results in the formation of the corresponding 2,2-dihalo-1-methanesulfonyloxy-8-phthalimido-4-p-toluenesulfonyl-4-aza-octane (19).

Reaction of (19) with potassium phthalimide in anhydrous dimethylformamide results in the preparation of 2,2-dihalo-1,8-diphthalimido-4-p-toluenesulfonyl-4-aza-octane (20). Heating (20) with hydrazine in a solvent such as ethanol serves to remove the phthaloyl protecting groups, whereas subsequently heating the product so obtained with aqueous HBr serves to remove the protecting tosyl moiety to yield the desired 2,2-dihalo-1,8-diamino-4-aza-octane (1) as their hydrobromide salts.

The compounds of the present invention are useful as antiproliferative and antitumor agents. The mechanism by which these compounds function is not known. What is known, however, is that when the compounds of this invention are added to a culture mediumm of growing rat hepatoma tissue culture (HTC) cells, they completely block the de novo synthesis of spermine. As a consequence of spermine depletion, a marked reduction of cell growth occurs. In combination with known ornithine decarboxylase inhibitors, such as 2-difluoromethyl-2,5-diaminopentanoic acid (DFMO) and [2R,5R]-6-heptyne-2,5-diamine (R,R-MAP), a more rapid and striking depletion of spermine is observed.

The compounds of this invention have also been found to be capable of slowing neoplastic cell proliferation when tested in standard animal tumor models. A preferred manner of utilizing these compounds is in combination with DFMO or [R,R]-MAP, or in combination with other therapeutic methods or agents known to affect polyamine metabolism in the treatment of neoplasms in animals. As used herein, the term animals is taken to mean warm blooded mammals, such as mice, rats, dogs, cats, guinea pigs, cows, horses and humans.

The compounds of this invention can be utilized both prophylactically and therapeutically. The amount of active ingredient for therapeutic administration can vary over a wide range and is dependent upon such factors as the species of animal to be treated, its age, health, sex, weight, nature and the severity of the condition being treated. Generally, a therapeutically effective amount of active ingredient to be administered will range from about 0.2 to 5 grams, and preferably from 0.5 to 3 grams per day. For prophylactic administration, corresponding lower doses of from 0.05 to 2 grams per day can be utilized.

When administered in combination with other ornithine decarboxylase inhibitors, such as DMFO or [R,R]-MAP, an amount of from 0.1 to 4 grams of the gem-dihalo-1,8-diamino-4-aza-octane and from 0.5 to 10 grams of the ornithine decarboxylase inhibitor are administered per day.

The compounds of this invention can be orally administered. Illustrative dosage levels for oral administration range from 2 to 500 mg per kg of body weight. Preferably, from 10 to 20 mg per kg of the gem-dihalo-1,8-diamino-4-aza-octane are orally administered per day in divided doses. In those instances where the drug is administered via the parenteral route, corresponding lower doses are employed. When administered in combination with ornithine decarboxylase inhibitors, the compounds can be administered in standard dosage unit forms, such as tablets, capsules, dragees, lozenges, elixirs, emulsions, suspensions and various intravenous, intramuscular or intradermal suspensions.

The preferred dosage form is that of a tablet or capsule. The amount of active ingredient contained in each dosage unit will, of course, vary depending upon the particular species of 7,7-dihalo-1,8-diamino-4-aza-octane employed, and the particular dosage form utilized. Generally, a given dosage unit will contain from 10 to 500 mg of the active ingredient in addition to the various pharmaceutical excipients contained therein. Tablets containing from 100 to 400 mg of the active ingredient, are the preferred dosage unit and can be administered b.i.d., or t.i.d. or q.i.d.

In preparing solid dose forms such as tablets, the active ingredient is generally blended with conventional pharmaceutical carriers or excipients such as gelatin, various starches, lactose, calcium phosphate or powdered sugar. The term pharmaceutical carrier as used herein also includes lubricants employed to improve the flow of tablet granulations and which prevent adhesion of tablet material to the surfaces of tablet dies and punches. Suitable lubricants include, for example, talc, stearic acid, calcium stearate, magnesium stearate and zinc stearate. Also included within the definition of a pharmaceutical carrier as used herein are disintegrating agents added to assist the breakup and dissolution of tablets following administration, as well as coloring and/or flavoring agents to enhance the aesthetic qualities of the tablets and make them more acceptable to the patient.

Suitable liquid excipients for the preparation of liquid dosage unit forms include water and alcohols such as ethanol, benzyl alcohol and the polyethylene alcohols, either with or without the addition of a surfactant. In general, the preferred liquid excipients particularly for injectable preparations, include water, saline solution, dextrose and glycol solutions such as an aqueous propylene glycol or an aqueous solution of polyethylene glycol. Liquid preparations to be used as sterile injectable solutions will ordinarily contain from about 0.5 to about 25% by weight, and preferably from about 1 to about 10% by weight, of the active ingredient in solution. In certain topical and parenteral preparations, various oils are utilized as carriers or excipients. Illustrative of such oils are mineral oils, glyceride oils such as lard oil, cod liver oil, peanut oil, sesame oil, corn oil and soybean oil. For insoluble compounds suspending agents may be added as well as agents to control the viscosity, as for example, magnesium aluminum silicate or carboxymethylcellulose. In addition to these excipients, buffers, preservatives and emulsifying agents may also be added.

The proportion of the active ingredient employed in parenteral dosage unit forms ranges from 0.05 to about 20% by weight, preferably from about 0.1 to about 10% by weight of the total liquid composition, the remaining component or components comprising any of the various pharmaceutical excipients previously mentioned. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above-identified HLB, or a mixture of two or more components having the desired HLB. Illustrative of surfactants useful in parenteral formulations are the class of polyoxyethylene sorbitan fatty acid esters as, for example, sorbitan monooleate and the high molecular weight adducts of ethylene oxide with a hydrophobic base, formed by the condensation of propylene oxide with propylene glycol.

The invention described herein is more particularly illustrated in conjunction with the following specific preparation, but is not necessarily limited thereto.

PREPARATION OF 7,7-DIFLUORO-1,8-DIAMINO-4-AZA-OCTANE

2,2-Difluoro-1,4-butanediol 2,2-Difluorosuccinic acid (120 g, 0.78 moles) and trifluoroacetic anhydride (540 mL) are refluxed (bath temperature 80° C.) for 2 hours. Most of the trifluoroacetic acid is distilled utilizing a short Vigreux column, the final traces are removed under vacuum (12 mm Hg, 50° C.) and finally by stripping twice with carbontetrachloride. The oily residue solidifies on scratching with petroleum ether. Filtration and washing with petroleum ether yields 2,2-difluorosuccinic anhydride as slightly violet crystals: 98 g (92%).

The 2,2-difluorosuccinic anhydride (98 g, 0.72 moles) is dissolved in chloromethane and slowly added with stirring to methanol, cooled in an ice bath. The mixture is kept at room temperature overnight, evaporated and stripped twice with carbon tetrachloride to yield methyl 2,2-difluorosuccinate as a slightly brownish oil: 121 g (100%).

In a 4 L flask equipped with a reflux condenser and 1 L dropping funnel, a solution of $BH_3.Me_2S$ complex (10M, 88 mL) in dry dicholoromethane (1 L) is slowly added over a 2 hour period to a stirred solution of the methyl 2,2-difluorosuccinate (120 g, 0.714 moles) in dry tetrahydrofuran at 20° C. After refluxing (bath temperature 80° C.) for about 15 hours, the mixture is allowed to cool to room temperature and methanol (1 L) is slowly added. Evaporation yields methyl 2,2-difluoro-4-hydroxybutyrate as an oil which is stripped with methanol (1 L) and finally with $CCl_4$ to yield a yellow oil: 100 g (92%).

To a cold (0° C.) solution of sodium borohydride (10.3 g, 0.272 moles) in ethanol, a solution of the methyl 2,2-difluoro-4-hydroxybutyrate (55 g, 0.36 moles) in ethanol is slowly added, while maintaining the internal temperature of the reaction mixture between −5° C. and 0° C. The mixture is stirred for 1 hour at 0° C., then, an approximately 4N solution of HCl gas in methanol (200 mL) is carefully added. Sodium chloride is filtered, the methanol is removed under vacuum, and the residue is dissolved in ethanol. Additional NaCl is again removed by filtration (membrane filter) and evaporation of the filtrate yields the compound 2,2-difluoro-1,4-butanediol as a colorless oil when distilled in a Kugelrhor at 150° C./0.05 mm Hg; 41 g (90%).

1-Benzyloxy-2,2-difluorobutylamine

Under nitrogen a tetrahydrofuran solution of 2,2-difluoro-1,4-butanediol (60 g, 0.476 moles) and benzyl bromide (81.8 g, 0.476 moles) is cooled in an ice salt bath to an internal temperature of −5° C. to 0° C. Solid potassium-tert.-butoxide (53.5 g, 0.477 moles) is added in portions, keeping the internal temperature at approximately 0° C. After stirring at room temperature overnight, the KBr is filtered off and the solvent is evaporated. The residue is dissolved in dichloromethane and washed with 1N HCl (twice) and with water (twice). Drying ($Na_2SO_4$) and subsequent evaporation yields an oil: 106 g (somewhat more than theory; some $CH_2Cl_2$ left).

The resulting material represents a mixture of 1-benzyloxy-2,2-difluoro-4-hydroxybutane and 1-benzyloxy-3,3-difluoro-4-hydroxybutane. Separation is performed by chromatography on silica (1 kg; eluent: ethyl acetate/pet. ether 20:80; fraction size: 250 mL). Fractions 17 to 19 contain 1-benzyloxy-3,3-difluoro-4-hydroxybutane (12.85 g, 12.5%), fractions 25 to 40 yield 1-benzyloxy-2,2-difluoro-4-hydroxybutane (45.85 g), and fractions 20–24 yield a mixture (27.6 g) both isomers. This mixture is again subjected to chromatography (1 Kg $SiO_2$, same eluent as above) to yield an additional 16 g of 1-benzyloxy-2,2-difluoro-4-hydroxybutane isomer as an oil for a total yield: 62 g (60%).

To a solution of 1-benzyloxy-2,2-difluoro-4-hydroxybutane (50 g, 0.231 moles) and dry pyridine (100 mL) in dichloromethane cooled in an ice bath, methanesulfonyl chloride (26.52 g, 0.232 moles) in dichloromethane (100 mL) is slowly added. After stirring at room temperature overnight, the mixture is washed with 2N HCl (2×1 L) and twice with water. Drying and subsequent evaporation of the solvent yields 1-benzyloxy-2,2-difluoro-4-methanesulfonyloxybutane as a yellow oil: 63.44 g (93%).

A mixture of 1-benzyloxy-2,2-difluoro-4-methanesulfonyloxybutane (63.44 g, 0.216 moles), potassium phthalimide (44 g, 0.238 moles) and dry DMF (500 mL), distilled from $CaH_2$) is stirred and heated at 100° C. After a short time the mixture solidifies, and an additional dry DMF (500 mL) is added. Upon heating at 90°–100° C. for another 20 hours, salts are removed by filtration, and the DMF is distilled under vacuum (oil pump). The residue is dissolved in $CH_2Cl_2$ (800 mL) and washed with 1N KOH (twice) and 1N HCl (twice). Drying ($Na_2SO_4$) and evaporation yields N-(4-benzyloxy-3,3-difluorobutyl)-phthalimide as a yellow oil: 68.5 g (92%).

The compound N-(4-benzyloxy-3,3-difluorobutyl)phthalimide (68.5 g, 198.6 mmoles) and hydrazine hydrate (10 g, 200 mmoles) are stirred and heated overnight in ethanol (200 mL) at 90°–100° C. A mixture of concentrated HCl (94 mL) and ethanol (1130 mL) is added, and heating (90°–100° C.) is continued for 1.5 hours. After cooling (ice bath), phthalhydrazide is removed by filtration, and the filtrate is evaporated. The residue is taken up in water and extracted with ether (2×500 mL). After filtration through a membrane filter (Millipore), evaporation of the filtrate yields white crystals. These are dissolved in ethanol, the solution is filtered (Millipore organic) and the filtrate is evaporated to yield a residue which crystallizes on addition of ether: 34 g (68%). Evaporation of the ether extracts yields a partially crystalline material (20 g) consisting of starting material. Repetition of the hydrazine cleavage upon this mixture yields a second crop of 4-benzyloxy-3,3-difluorobutylamine (9.1 g). Total: 43.2 g (86.5%).

1-Phthalimido-4-p-toluenesulfonyl-7,7-difluoro-8-benzyloxy-4-aza-octane

The compound 4-benzyloxy-3,3-difluorobutylamine, triethylamine (37 g, 0.37 moles, and p-toluenesulfonyl chloride (33.8 g, 0.177 moles) are stirred in dry dichloromethane (600 mL) at room temperature overnight. The solution is washed with 1N HCl (250 mL), water (250 mL), dried ($Na_2SO_4$) and evaporated to yield N-(4-benzyloxy-3,3-difluorobutyl)-p-toluenesulfonylamide as a solid 63.17 g (99.5%).

To a solution of N-(4-benzyloxy-3,3-difluorobutyl)-p-toluenesulfonamide (63.17 g, 171.2 mmoles) and sodium iodide (3 g) in dry dimethylformamide (400 mL) is added solid potassium tert.-butoxide (19.2 g, 171 mmoles) with stirring at room temperature. The compound 3-bromopropylphthalimide (46 g, 171 mmoles) is added, and the mixture is stirred at room temperature overnight. The salts are filtered, and the filtrate is evaporated to dryness. The residue is taken up in dichloromethane (500 mL), filtered, and evaporated to dryness. Dissolving in ether (750 mL), washing with aqueous sodium bisulfite (10 g/250 mL), water (3×400 mL), drying ($Na_2SO_4$) and evaporation yields 1-phthalimido-4-p-toluenesulfonyl-7,7-difluoro-8-benzyloxy-4-aza-octane as a yellow oil (95.0 g, 99.8%). Traces of ether are removed by stripping twice with chloroform prior to using the material for the next step.

7,7-difluoro-1,8-diamino-4-aza-octane

Under nitrogen, trimethylsilyliodide (26 mL, 182.8 mmoles) dissolved in dry dichloromethane (100 mL), is slowly added to a stirred solution of 1-phthalimido-4-p-toluenesulfonyl-7,7-difluoro-8-benzyloxy-4-aza-octane (95.0 g, 170.8 mmoles) in dichloromethane at room temperature. After stirring overnight at room temperature, triethylamine (25 g, 0.25 moles) is slowly added, and stirring is continued for one hour. The mixture is washed with 1N HCl (500 mL), 10% aqueous $NaHSO_3$ (250 mL), and water (2×250 mL). Drying ($Na_2SO_4$) gives a brown oil (83.8 g) which, according to NMR, is primarily the O-trimethyl-silyl derivative of 1-phthalimido-4-p-toluenesulfonyl-7,7-difluoro-8-hydroxy-4-aza-octane. This oil is dissolved in methanol (100 mL), and a few drops of a saturated solution of HCl gas in ether are added, whereupon crystallization occurs. The nearly white crystals of 1-phthalimido-4-p-toluenesulfonyl-7,7-difluoro-8-hydroxy-4-aza-octane are collected and washed with petroleum ether: 56.0 g (70.4%).

To a solution of 1-phthalimido-4-p-toluenesulfonyl-7,7-difluoro-8-hydroxy-4-aza-octane (56.0 g, 120 mmoles) and dry pyridine (50 mL) in dry dichloromethane (400 mL), a solution of methanesulfonylchloride (14.4 g, 1.05 equivalents) in dichloromethane is added slowly at room temperature. After stirring overnight at room temperature, the mixture is washed with 1N HCl (500 mL), 10% aqueous $NaHSO_3$ (250 mL), and water (250 mL). Drying ($Na_2SO_4$) and evaporation of the solvent yields an oil which solidifies under oil pump vacuum. Digestion with an acetone/cyclo-hexane mixture gives colorless crystals of 1-phthalimido-4-p-toluenesulfonyl-7,7-difluoro-8-methanesulfonyloxy-4-aza-octane.

The compound 1-phthalimido-4-p-toluenesulfonyl-7,7-difluoro-8-methanesulfonyloxy-4-aza-octane (61.18 g, 112.5 mmoles), potassium phthalimide (30.5 g, 165 mmoles) and dry dimethylformamide (500 mL) are stirred and heated at 120° C. for 72 hours. After cooling, the salts are removed by filtration, and the solvent is removed under vacuum. The residue is taken up in dichloromethane (500 mL) and washed with 2N NaOH (350 mL, emulsions) and water (2×350 mL). Drying ($Na_2SO_4$) and evaporation yields an oil which on stripping with chloroform/cyclohexane provides a solid foam: 58.95 g (88%), hygroscopic, consisting of 1,8-diphthalimido-4-p-toluenesulfonyl-7,7-difluoro-4-azaoctane.

The compound 1,8-diphthalimido-4-p-toluenesulfonyl-7,7-difluoro-4-aza-octane (58.95 g, 99.07 moles) and 1M hydrazine hydrate in ethanol (235 mL, 235 mmoles) are stirred and heated at 90° C. overnight. Conc. HCl (150 mL) is added, and heating (90° C.) and stirring are continued for 45 min. After cooling to room temperature, phthalhydrazide is removed by filtration, and the solvent is evaporated. The residue is dissolved in water, the solution is filtered and evaporated to yield a residue which solidifies upon stripping with acetone. This material is dissolved in water (300 mL), aqueous NaOH (25 g NaOH/150 mL water) is added, and the mixture is extracted with dichloromethane (3×400 mL). Washing with water (200 mL), drying ($Na_2SO_4$) and evaporation of the solvent yields a yellow oil, 35.0 g, which is dissolved in 6N HCl (300 mL), evaporated, and stripped with ethanol (twice), $CCl_4$ (twice) and acetone (twice) to yield 1,8-diamino-4-p-toluenesulfonyl-7,7-difluoro-4-aza-octane as a white solid. This compound is recrystallized by dissolving in the minimum amount of methanol and the addition of acetone/ether: 31.3 g (78%).

The 1,8-diamino-4-p-toluenesulfonyl-7,7-difluoro-4-aza-octane so obtained is refluxed with 100 mL of 48% aqueous HBr for 20 hours. After cooling to room temperature, the solution is carefully extracted with ether (5×300 mL). After evaporation of the solvent, traces of free HBr are removed by stripping twice with water; on stripping with ethanol, the desired 7,7-difluoro-1,8-diamino-aza-octane crystallizes as the trihydrobromide. Digestion with acetone yields white crystals which are washed with acetone, a small amount of ethanol, and finally with ether: 12.85 g (95%).

Anal. Calc'd for $C_7H_{20}Br_3F_2N_3$: C, 19.83; H, 4.75; N, 9.91. Found: C, 19.83; H, 4.58; N, 9.93.

PREPARATION OF 6,6-DIFLUORO-1,8-DIAMINO-4-AZA-OCTANE

1-Benzyloxy-3,3-difluorobutylamine

The compound 1-benzyloxy-3,3-difluoro-4-hydroxybutane (17 g, 78.7 mM), obtained as described in the previous Example for the preparation of 4-benzyloxy-3,3-difluorobutylamine, is dissolved in dry pyridine (35 mL) and dichloromethane (100 mL), and methanesulfonyl chloride (9 g, 78.6 mM) is added slowly with stirring. The mixture is maintained at room temperature overnight. Following the addition of more dichloromethane, the mixture is washed with 1N HCl (twice), water (twice) and dried over $Na_2SO_4$. The solution is evaporated to yield 1-methanesulfonyloxy-2,2-difluoro-4-benzyloxybutane as an oil: 22.8 g (98%).

The compound 1-methanesulfonyloxy-2,2-difluoro-4-benzyloxybutane (21.8 g 74.1 mM), dry DMF (100 mL), and potassium phthalimide (15.26 g, 10% excess) are stirred and heated under nitrogen, at 120° C. for 5 days. Following the addition of water (500 mL), the mixture is extracted with ether. The organic phase is washed with 1N CCl followed by water (twice), dried ($Na_2SO_4$) and concentrated to a volume of about 100 mL. Upon addition of petroleum ether, crystallization occurs. After chilling for 3 hours at 5° C., beige crystals of the compound N-(4-benzyloxy-2,2-difluorobutyl)phthalimide are obtained, filtered and washed with petroleum ether: 18 g (70%).

The compound N-(4-benzyloxy-2,2-difluorobutyl)phthalimide (8.97 g, 26 mM) and a 1M solution of hydrazine hydrate in ethanol (26 mL) are stirred under reflux. After a few minutes, a heavy precipitate is observed. Stirring and heating (bath temperature: 90°–100° C.) are continued overnight. Ethanol (220 mL) and concentrated HCl (18 mL) are added, and the mixture is refluxed for an additional 1½ hour. After cooling (ice) the phthaloyl hydrazide is filtered, and the filtrate is evaporated. The residue is dissolved in water, filtered, and the solution is again evaporated. Residual water is removed by stripping with ethanol (twice) and $CCl_4$ (twice). The residue is dissolved in a minimum amount of ethanol. Crystallization occurs upon the addition of water, which after chilling to 5° C. yields white crystals of 4-benzyloxy-2,2-difluorobutylamine as the hydrochloride salt: 5.16 g (79%).

1-Phthalimido-4-p-toluenesulfonyl-6-6-difluoro-8-benzyloxy-4-aza-octane

To a solution of 4-benzyloxy-2,2-difluorobutylamine (5.16 g, 20.5 mM) and triethylamine (4.4 g, 43.4 mM) in dry dichloromethane is added toluenesulfonyl chloride (4.14 g, 21.7 moles). The mixture is stirred at room temperature overnight. Additional dichloromethane is added, and the organic phase is washed with 1N HCl followed by a water wash. Drying ($Na_2SO_4$) and evaporation of the solvent yields a white solid which is dissolved in a small volume of ether. Addition of petroleum ether yields the compound, N-(4-benzyloxy-2,2-difluorobutyl)-p-toluenesulfonamide as white crystals: 7.0 g (92%).

To a solution of N-(4-benzyloxy-2,2-difluorobutyl)-p-toluenesulfonamide (7.0 g, 19 mM) in dry DMF (20 mL), is added potassium-tert.-butoxide (2.34 g, 21 mmoles), and the mixture is stirred for 30 minutes. To this mixture are added N-3-bromopropyl-phthalimide (5.1 g, 19 mmoles) and sodium iodide (0.33 g), and the entire mixture is then stirred overnight under nitrogen at room temperature. Following the addition of brine, the mixture is extracted with ether, washed with 1N HCl (twice), then with brine (twice), and dried over $Na_2SO_4$. Evaporation of the solvent yields 1-phthalimido-4-p-toluenesulfonyl-6,6-difluoro-8-benzyloxy-4-aza-octane as an oil, which crystallizes on scratching with ether/petroleum ether to form white crytals: 9.5 g (90%).

1-Phthalimido-4-p-toluenesulfonyl-6,6-difluoro-8-methanesulfonyloxy-4-aza-octane A solution of 1-phthalimido-4-p-toluenesulfonyl-6,6-difluoro-8-benzyloxy-4-aza-octane (9.5 g, 17.1 mM) and trimethylsilyl iodide (2.7 mL, 10% excess) in dry dichloromethane is stirred overnight at room temperature under nitrogen. Triethylamine (3 g) is added, and stirring is continued for 1 hour at room temperature. Following the addition of more dichloromethane, the reaction mixture is washed with 1N HCL (twice), aqueous $NaHSO_3$ (twice), brine (twice), and dried ($Na_2SO_4$). The solvents are removed by evaporation to yield an oil. This oil is dissolved in methanol and 1 mL of a 9N solution of HCL in methanol is added. The mixture is evaporated and stripped twice with $CCl_4$ to provide an oil, which upon scratching with ether/petroleum ether yields 1-phthalimido-4-p-toluenesulfonyl-6,6-difluoro-8-hydroxy-4-aza-octane as slightly violet crystals: 6.8 g (85%).

To a mixture of 1-phthalimido-4-p-toluenesulfonyl-6,6-difluoro-8-hydroxy-4-aza-octane (6.75 g 14.5 mM), dry dichloromethane (25 mL) and dry pyridine (10 mL), a solution of methanesulfonyl chloride (1.7 g) in dichloromethane (25 mL) is slowly added with stirring. The reaction mixture is kept at room temperature overnight, additional dichloromethane is added, and the reaction mixture is washed with 1N HCl (twice) and then washed with brine (twice). The resulting solution is dried ($Na_2SO_4$) and the solvent evaporated to yield an oil. Upon scratching this oil with ether/petroleum ether, the compound 1-phthalimido-4-p-toluenesulfonyl-6,6-difluoro-8-methanesulfonyloxy-4-aza-octane is obtained as white crystals: 7.64 g (97%).

6,6-Difluoro-1,8-diamino-4-aza-octane

Under an atmosphere of nitrogen, a mixture of 1-phthalimido-4-p-toluenesulfonyl-6,6-difluoro-8-methanesulfonyloxy-4-aza-octane, (7.6 g, 14 mM), potassium phthalimide (2.85 g, 10% excess) and dry DMF (20 mL) is stirred and heated at 90° C. for 20 hours. Following the addition of water (approximately 100 mL), the reaction is extracted with dichloromethane, washed with 1N KOH (twice), and dried ($Na_2SO_4$). The solvents are removed by evaporation to yield and oil (8.7 g) which is flash-chromatographed on silica (300 g, eluent: ethyl acetate/petroleum ether/50—50) with 100 mL fractions being taken. Fractions 15–29 are pooled and the solvent is evaporated to yield 1,8-diphthalimido-4-p-toluenesulfonyl-6,6-difluoro-4-aza-octane, which crystallizes on standing: 6.62 g (80%).

The 1,8-diphthalimido-4-p-toluenesulfonyl-6,6-difluoro-4-aza-octane so obtained (6.62 g, 11.1 mM) together with a 1M solution of hydrazine hydrate in ethanol (22.5 mL) are stirred under nitrogen overnight at 100° C. The solvent is removed under reduced pressure, and the residue is refluxed with ethanol (30 mL) and concentrated HCl (30 mL) for 1½ hours. After cooling (ice), the phthalyl hydrazide is filtered, and the filtrate evaporated. The residue is taken up in water (20 mL) and filtered through a membrane filter (Millipore). The filtrate is washed with water, the solvents are evaporated and the residue is stripped with ethanol (twice) and $CCl_4$ (twice). Following the addition of acetone, the product 1,8-diamino-4-p-toluenesulfonyl-6,6-difluoro-4-aza-octane begins to crystallize, which is completed upon the addition of ether to yeild slightly beige-colored crystals: 4.6 g (yield quantitative).

The 1,8-diamino-4-p-toluenesulfonyl-6,6-difluoro-4-aza-octane so obtained (4.6 g) is heated with 47% aqueous HBr (100 mL) at 100° C. (bath temperature) for 20 hours. After cooling with ice, the solution is extracted 3 times with ether. The aqueous solution is evaporated, and the residue is stripped with water (twice), CCl$_4$ (twice), and ethanol (twice). The residue is digested with a small amount of ethanol and acetone to induce crystallization. The crystals so obtained are washed with ethanol, acetone and ether to yield the desired 1-diamino-6,6-difluoro-4-aza-octane as white crystals, 4.2 g (88%).

Anal. Calc'd for C$_7$H$_{20}$Br$_3$F$_2$N$_3$: C, 19.83; H, 4.75; N, 9.91. Found: C, 19.70; H, 4.50; N, 9.83.

PREPARATION OF 2,2-DIFLUORO-1,8-DIAMINO-4-AZA-OCTANE

1-Phthalimido-2,2-difluoro-3-butene

To a stirred mixture of 2,2-difluoro-1,4-butanediol (12.97 g, 103 mM), dry pyridine (65 mL) and dichloromethane (200 mL) is slowly added a solution of methanesulfonylchloride (23.6 g) in dichloromethane (50 mL). Stirring is continued overnight. The reaction mixture is washed with 2N HCl (twice), followed by 10% aqueous NaHCl$_3$ until neutral, and then with water. The organic layer is dried (MgSO$_4$) and upon evaporation of the solvents, a slightly yellow oil is obtained. Crystallization is induced by scratching the oil with dry ether, to yield the compound 1,4-bis-methanesulfonyloxy-2,2-difluorobutane as white crystals: 22.3 g (77%).

The compound 1,4-bis-methanesulfonyloxy-2,2-difluorobutane (20 g, 71 mM) and diazabicycloundecene (21.6 g, 142 mM) are stirred with dry tetrahydrofuran (150 mL) and heated overnight at 80° C. under nitrogen. The solvents are removed under vacuum, and the residual oil is dissolved in dichloromethane, washed with 1N HCl (twice), brine (twice) and dried (Na$_2$SO$_4$). Evaporation of the solvents yields the compound 1-methanesulfonyl-2,2-difluoro-3-butene as an oil: 11.2 g (85%).

The compound 1-methanesulfonyl-2,2-difluoro-3-butene (11.2 g, 60.2 mM), potassium phthalide (12.3 g, 66.4 mM) and dry dimethylformamide (30 mL) are stirred and heated (bath temperature 110° C.) under nitrogen for 120 hours. After cooling to room temperature, the crude reaction product is precipitated by the addition of water (approximately 300 mL), filtered and dissolved in dichloromethane. The dichloromethane solution is washed with 1N potassium hydroxide (twice), water (twice), dried (Na$_2$SO$_4$) and evaporated to yield 1-phthalimido-2,2-difluoro-3-butene as beige-colored crystals: 11.9 g (83%).

1-p-Toluenesulfonamino-2,2-difluoro-3-butene

The compound 1-phthalimido-2,2-difluoro-3-butene (11.4 g, 48.1 mM) is heated for 20 hours. After cooling in an ice bath, the phthalic acid is removed via filtration and the filtrate evaporated. The residue so obtained is dissolved in water, extracted with ether (twice), evaporated to dryness and stripped with isopropanol. Trituration with ether yields hygroscopic crystals of 1-amino-2,2-difluoro-3-butene as the hydrochloride salt: 6.12 g, (88%).

To a stirred mixture of 1-amino-2,2-difluoro-3-butene hydrochloride (6.1 g, 42.5 mM), 50 mL of dry dichloromethane and triethylamine (8.74 g, 2 equivalents) all of which have been cooled in an ice bath, is slowly added a solution of tosyl chloride (8.1 g, 1 equivalent) in 50 mL of dichloromethane. Stirring is continued overnight at room temperature, additional dichloromethane is added to the reaction mixture, and the resulting organic layer is washed wit 1N HCl (twice), water (twice) and dried (Na$_2$SO$_4$). Evaporation of the solvent yields a brown semi-solid material (9.66 g), which is purified via flash chromatography on silica (300 g, eluent: ethyl acetate/petroleum ether 20–80; fraction size 100 mL). Fractions 17–25 are combined and evaporated to yield 1-p-toluenesulfonamino-2,2-difluoro-3-butene as white crystals; 4.8 g (43%). The desired compound can be recrystallized from ether/petroleum ether to yield very fine, cotton-like, needles.

Anal. Calc'd for C$_{11}$H$_{13}$F$_2$NO$_2$S: C, 50.56; H, 5.02; N, 5.36. Found: C, 50.93; H, 5.02; N, 5.45.

Following essentially the same procedure for the preparation of the 7,7-difluoro-1,8-diamino-4-aza-octane and the 6,6-difluoro-1,8-diamino-4-aza-octane viz, alkylating the 1-methanesulfonyl-2,2-difluorobutene with 4-bromo-butylphthalimide; oxidizing the double bond to the carboxylic acid; reducing the carboxylic acid to a primary alcohol with borane-methylsulfide complex; mesylating the primary alcohol; reacting the mesyl derivative with potassium phthalimide to obtain the corresponding 1,8-diphthalimido derivative; and removing the phthaloyl and tosyl protecting groups; the desired compound, 2,2-difluoro-1,8-diamino-4-aza-octane, is obtained.

DEMONSTRATION OF THE ANTIPROLIFERATIVE EFFECT OF 7,7-DIFLUORO-1,8-DIAMINO-4-AZA-OCTANE

Morris rat hepatoma 7288C (HTC) cells are routinely grown as a suspension culture in Swim's 77 medium supplemented with 10% (V/V) dialysed horse serum, 11.0 mM glucose, 2 mM glutamine, 0.057 mM cystine, 5.9 mM NaHCO$_3$ and 50 mM of N-tris(hydroxymethyl)-methylglycine. The HTC cell cultures are incubated in the presence or absence of 10 μm of the compound 7,7-difluoro-1,8-diamino-4-aza-octane and observed for a period of 11 days.

The cell culture medium is changed at days 2, 4, 7 and 9 to maintain cells in a logarithmic phase of growth. The actual cell numbers are determined by cell-counting and the relative cell growth is calculated taking into account the various dilution factors employed. The percent inhibition of cell growth is calculated according to the equation:

$$100 - 100\, \frac{N_t n - N_t O}{N_c n - N_c O}$$

wherein

N$_c$O is the relative growth of control cultures at time=0

N$_c$n is the relative growth of control cultures at time=n

N$_t$O is the relative growth of test cultures at time=0, and

N$_t$n is the relative growth of test cultures at time=n.

The cloning efficiency is a measure of viability used to determine whether the test compound functions as a cytostatic or cytotoxic agent. The cloning efficiency is determined by seeding 0.25–1.25×10$^3$ cells in 60 mm plastic petri-dishes each containing 5 ml of the following cloning medium: Swim's 77 medium supplemented with 10% (V/V) horse serum, 11 mM glucose, 2 mM glutamine, 0.057 mM cystine, 1.8 mM CaCl$_2$, 17.5 mM NaHCO$_3$ and 1 mM N-tris(hydroxymethyl)methylglycine. The petri-dishes are incubated at 37° C. in a humidified incubator under CO$_2$/air atmosphere (5% V/V) for 12 days, and the viable cell colonies are counted at that time and compared to control. The results are expressed as percent inhibition of viable cell colonies.

Table I illustrates that administration of 10 μM of 7,7-difluoro-1,8-diamino-4-aza-octane to the culture medium inhibits cell growth by 97% at the end of 11 days. Additionally, four days following the addition of the test compound, cell viability was decreased by 72%.

TABLE I

Effects of 7,7-Difluoro-1,8-Diamino-4-Aza-Octane On HTC Cell Growth And Viability

| Time (days) | Relative Growth | | (%) Inhibition Cell Growth | (%) Inhibition of Viable Cell Colonies |
|---|---|---|---|---|
| | Control | Test Compound | | |
| 0 | 1.00 | 1.00 | 0 | — |
| 1 | 1.83 | 1.46 | 45 | 21 |
| 2 | 3.67 | 2.92 | 28 | — |
| 3 | 7.29 | 5.57 | 27 | — |
| 4 | 14.1 | 5.99 | 62 | 42 |
| 5 | — | — | — | — |
| 6 | 55.8 | 12.5 | 78 | 72 |
| 7 | 100 | 13.4 | 87 | — |
| 8 | 209 | 18.9 | 91 | — |
| 9 | 362 | 20.7 | 95 | — |
| 10 | 747 | 26.1 | 97 | — |
| 11 | 1133 | 30.2 | 97 | — |

Table II illustrates the effects of the compound 7,7-difluoro-1,8-diamino-4-aza-octane (Compound A) in combination with the irreversible L-ornithine decarboxylase inhibitor, [2R,5R]-6-heptyne-2,5-diamine (Compound B). This experiment indicates that the antiproliferative effects, obtained upon administration of 100 μM of [2R,5R]-6-heptyne-2,5-diamine to the culture medium are enhanced by the presence of 10 μM of 7,7-difluoro-1,8-diamino-4-aza-octane. Thus, for example, cell viabilty of the combination was decreased by 44% by the end of day 1.

Table III illustrates the effects of 10 μM of the compound 7,7-fluoro-1,8-diamino-4-aza-octane (Compound A) in combination with 5 mM of the irreversible L-ornithine decarboxylase inhibitor, DL-α-difluoromethylornithine (Compound C). This experiment illustrates that the antiproliferative effects obtained with the combination of Compounds A and C were greater than the antiproliferative effects obtained for either Compound A or Compound C when used alone.

TABLE III

Effects of 7,7-Difluoro-1,8-Diamino-4-Aza-Octane (A) In Combination With DL-α-Difluoromethylornithine (C) On HTC Cell Growth And Viability

| Time (days) | Relative Growth | | | (%) Inhibition of Cell Growth | |
|---|---|---|---|---|---|
| | Control | Compound C | Compounds A + C | Compound C | Compounds A + C |
| 0 | 1.00 | 1.00 | 1.00 | 0 | 0 |
| 1 | 1.92 | 1.92 | 1.58 | 0 | 37 |
| 2 | 3.82 | 2.58 | 1.97 | 44 | 66 |
| 3 | 7.35 | 3.51 | 2.61 | 61 | 75 |
| 4 | 14.60 | 4.49 | 2.43 | 74 | 89 |

I claim:

1. A process for the preparation of gem-dihalo-1,8-diamino-4-aza-octane derivatives having the formula:

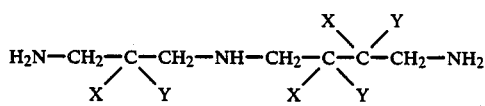

wherein X and Y represent hydrogen or halogen with the proviso that both halogens are substituted on one and only one carbon atom at any given time which comprises:

(1) in the case of the 6,6-dihalo or 7,7-dihalo derivatives
 (a) reacting 2,2-dihalo-1,4-butanediol having the formula

TABLE II

Effects of 7,7-Difluoro-1,8-Diamino-4-Aza-Octane (A) In Combination With [2R,5R]-6-Heptyne-2,5-Diamine (B) On HTC Cell Growth And Viability

| Time (days) | Relative Growth | | | (%) Inhibition of Cell Growth | | (%) Inhibition of Viable Cell Colonies | |
|---|---|---|---|---|---|---|---|
| | Control | Compound B | Compounds A + B | Compound B | Compounds A + B | Compound B | Compound A + B |
| 0 | 1.00 | 1.00 | 1.00 | 0 | 0 | 0 | 0 |
| 1 | 1.92 | 1.91 | 1.63 | 0 | 31 | 1 | 44 |
| 2 | 3.82 | 2.47 | 2.08 | 48 | 62 | 22 | 69 |
| 3 | 7.35 | 3.51 | 2.52 | 60 | 76 | 3 | 77 |
| 4 | 14.60 | 4.26 | 2.70 | 76 | 88 | 52 | 89 |

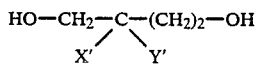

wherein X' and Y' are chlorine or fluorine, with benzyl bromide to form a mixture of the corresponding 1-benzyloxy-2,2-dihalo-4-hydroxybutane and 1-benzyloxy-3,3-dihalo-4-hydroxybutane as represented by the formula

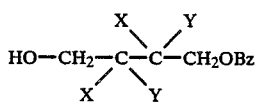

wherein X and Y are as described above and Bz represents the benzyl group;

(b) separating said isomers, reacting the free hydroxyl group with methanesulfonyl chloride, and reacting the 1-benzyloxy-gem-dihalo-4-methanesulfonyloxybutane so obtained with potassium phthalimide to obtain the corresponding N-(4-benzyloxy-gem-dihalobutyl)phthalimide derivative having the formula

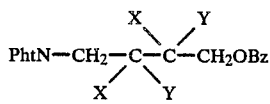

wherein Pht represents the phthaloyl group;

(c) reacting said phthalimide with hydrazine to form the corresponding 4-benzyloxy-gem-dihalobutylamine, protecting the free amine with p-toluenesulfonyl choride to form the corresponding N-(4-benzyloxy-gem-dihalobutyl)-p-toluenesulfonamide derivative having the formula

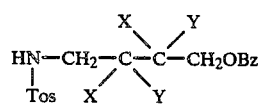

wherein Tos represents the p-toluenesulfonyl group;

(d) alkylating said p-toluenesulfonamide derivative with 3-bromopropylphthalimide to form the corresponding 1-phthalimido-4-p-toluenesulfonyl-gem-dihalo-8-benzyloxy-4-aza-octane derivative having the formula

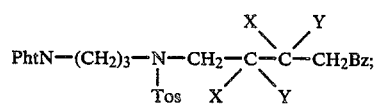

(e) cleaving said benzyloxy group to form the primary alcohol, reacting said primary alcohol with methanesulfonyl chloride and reacting the 1-phthalimido-4-p-toluenesulfonyl-gem-dihalo-8-methanesulfonyloxy-4-aza-octane so obtained with potassium phthalimide to obtain the corresponding 1,8-diphthalimido-4-p-toluenesulfonyl-gem-dihalo-4-aza-octane derivative having the formula

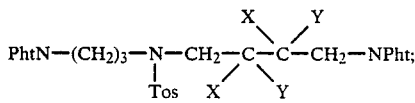

(f) heating said 1,8-diphthalimido-4-p-toluenesulfonyl-gem-dihalo-4-aza-octane with hydrazine in ethanol to remove the phthaloyl protecting groups, followed by heating with aqueous HBr to remove the tosyl protecting group to obtain the desired 6,6- or 7,7-dihalo-1,8-diamino-4-aza-octane derivatives having the formula

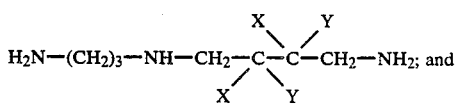

(2) in the case of the 2,2-dihalo derivatives:

(a) reacting said 2,2-dihalo-1,4-butanediol with two equivalents of methanesulfonyl chloride to form the corresponding 1,4-bis-methanesulfonyloxy-2,2-dihalobutyl, heating with diazabicycloundecen to prepare the corresponding 1-methanesulfonyloxy-2,2-dihalo-3-butene having the formula

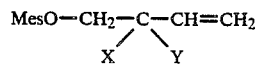

wherein Mes represents the methanesulfonyl group;

(b) reacting said 1-methanesulfonyloxy derivative with potassium phthalimide and cleaving the resulting phthaloyl moiety to yield the corresponding 2,2-dihalo-3-butenylamine having the formula

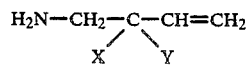

(c) protecting said amine with p-toluenesulfonyl chloride and alkylating said protected derivative with 4-bromobutylphthalimide to yield the corresponding N-(4-phthalimidobutyl)-N-(2,2-dihalo-3-butenyl)-p-toluenesulfonamide having the formula

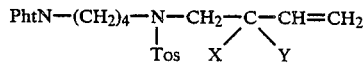

(d) oxidizing the double bond of said N-(4-phthalimidobutyl) derivative, followed by reduction with borane-methylsulfide complex to form the corresponding 8-phthalimido-4-p-toluenesulfonyl-2,2-dihalo-4-aza-octanol having the formula

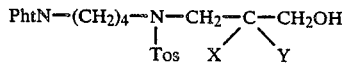

(e) reacting said 2,2-dihalo-4-aza-octanol derivative with methanesulfonyl chloride to form the corresponding 1-methanesulfonyloxy-8-phthalimido-4-p-toluenesulfonyl-4-aza-octane and reacting with potassium phthalimide to obtain the corresponding 2,2-dihalo-1,8-diphthalimido-4-p-toluenesulfonyl-4-aza-octane having the formula

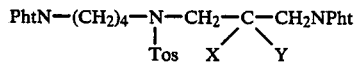

(f) heating with hydrazine in ethanol to remove the phthaloyl protecting groups, followed by heating with aqueous HBr to remove the tosyl protecting group to obtain the desired 2,2-dihalo-1,8-diamino-4-aza-octane derivatives having the formula

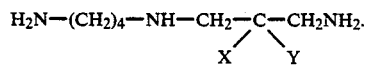

2. A process according to claim 1 wherein the compounds prepared are 6,6-dihalo or 7,7-dihalo-1,8-diamino-4-aza-octane derivatives.

3. A process according to claim 1 wherein the compounds prepared are 2,2-dihalo-1,8-diamino-4-aza-octane derivatives.

* * * * *

UNITED STATES PATENT AND TRADEMARK OFFICE
CERTIFICATE OF CORRECTION

PATENT NO. : 4,914,240

DATED : April 3, 1990

INVENTOR(S) : Fritz Gerhart and Pierre Mamont

It is certified that error appears in the above-identified patent and that said Letters Patent is hereby corrected as shown below:

At column 1, line 25, the patent reads "decarboxylatedS" and should read --decarboxylated-S--. At column 1, line 33, the patent reads "and and/or" and should read --and/or--. At column 1, line 35, the patent reads "inhibitors or S-adenosyl" and should read --inhibitors of S-adenosyl--. At column 1, line 54, the patent reads "4-azaoctane" and should read --4-aza-octane--. At column 3, line 65, the patent reads "benzylidene," and should read --benzylhalide,--. At column 7, line 44, the patent reads "mediumm" and should read --medium--. At column 8, line 8, the patent reads "DMFO" and should read --DFMO--. At column 10, lines 8-9, the patent reads "Kugelrhor" and should read --Kugelrohr--. At column 15, line 44, the patent reads "strirred" and should read --stirred--. At column 16, line 4, the patent reads "washed wit" and should read --washed with--.

Signed and Sealed this

Twenty-second Day of December, 1992

Attest:

DOUGLAS B. COMER

Attesting Officer

Acting Commissioner of Patents and Trademarks